US009161802B2

(12) United States Patent
Przybyszewski

(10) Patent No.: US 9,161,802 B2
(45) Date of Patent: Oct. 20, 2015

(54) PATTERNED ELECTRODES FOR TISSUE TREATMENT SYSTEMS

(71) Applicant: Solta Medical, Inc., Hayward, CA (US)

(72) Inventor: Piotr J. Przybyszewski, Fremont, CA (US)

(73) Assignee: SOLTA MEDICAL, INC., Hayward, CA (US)

( * ) Notice: Subject to any disclaimer, the term of this patent is extended or adjusted under 35 U.S.C. 154(b) by 235 days.

(21) Appl. No.: 13/733,642

(22) Filed: Jan. 3, 2013

(65) Prior Publication Data
US 2014/0188099 A1 Jul. 3, 2014

(51) Int. Cl.
*A61F 7/00* (2006.01)
*A61B 18/14* (2006.01)
*A61B 18/00* (2006.01)

(52) U.S. Cl.
CPC ......... *A61B 18/14* (2013.01); *A61B 2018/0016* (2013.01); *A61B 2018/00029* (2013.01); *A61B 2018/0047* (2013.01)

(58) Field of Classification Search
CPC ............... A61B 10/203; A61B 2018/0016; A61B 2018/0047; A61B 2018/00029; A61B 18/14; A61N 1/0492; A61N 1/0476; A61F 2007/0242
USPC ............ 606/9, 33, 41, 45, 46, 49; 607/98, 99, 607/115, 149–151; 600/372–374
See application file for complete search history.

(56) References Cited

U.S. PATENT DOCUMENTS

| 4,182,795 | A | * | 1/1980 | Baker et al. | 429/433 |
| 4,736,752 | A | * | 4/1988 | Munck et al. | 607/152 |
| 5,151,102 | A | * | 9/1992 | Kamiyama et al. | 606/51 |
| 5,562,720 | A | * | 10/1996 | Stern et al. | 607/98 |
| 5,713,942 | A | | 2/1998 | Stern et al. | |
| 5,919,188 | A | * | 7/1999 | Shearon et al. | 606/41 |
| 6,080,151 | A | * | 6/2000 | Swartz et al. | 606/45 |
| 6,169,926 | B1 | * | 1/2001 | Baker | 607/99 |
| 6,228,078 | B1 | * | 5/2001 | Eggers et al. | 606/32 |
| 6,345,196 | B1 | * | 2/2002 | Castelli | 600/509 |
| 6,512,945 | B1 | | 1/2003 | Hoium et al. | |
| 6,532,379 | B2 | * | 3/2003 | Stratbucker | 600/382 |
| 6,546,292 | B1 | * | 4/2003 | Steinhaus et al. | 607/116 |
| 6,850,795 | B2 | | 2/2005 | Hoium et al. | |
| 7,056,297 | B2 | | 6/2006 | Dohno et al. | |
| 7,135,034 | B2 | * | 11/2006 | Friedman et al. | 607/88 |
| 7,255,579 | B2 | * | 8/2007 | Sato et al. | 439/91 |
| 7,267,675 | B2 | | 9/2007 | Stern et al. | |
| 7,452,358 | B2 | | 11/2008 | Stern et al. | |
| 7,715,921 | B2 | | 5/2010 | Palti | |
| 8,086,322 | B2 | * | 12/2011 | Schouenborg | 607/115 |
| 8,221,410 | B2 | * | 7/2012 | Knowlton et al. | 606/41 |
| 8,323,277 | B2 | * | 12/2012 | Vilims | 606/41 |
| 8,506,506 | B2 | * | 8/2013 | Nebrigic et al. | 601/15 |
| 2004/0153057 | A1 | * | 8/2004 | Davison | 606/41 |
| 2005/0021118 | A1 | * | 1/2005 | Genau et al. | 607/116 |

(Continued)

*Primary Examiner* — Joseph Stoklosa
*Assistant Examiner* — Yasamin Ekrami
(74) *Attorney, Agent, or Firm* — Thompson Hine LLP; Toan P. Vo, Esq.

(57) ABSTRACT

Methods, apparatus, and systems for treating tissue located beneath a tissue surface with electromagnetic energy delivered from a treatment electrode. The treatment electrode may include a conductive layer and a plurality of openings extending through the conductive layer. The openings may vary in size or area across the conductive layer, and may vary progressively in size or area with location relative to the electrode perimeter.

19 Claims, 7 Drawing Sheets

(56) References Cited

U.S. PATENT DOCUMENTS

| | | |
|---|---|---|
| 2005/0251134 A1* | 11/2005 | Woloszko et al. ............. 606/46 |
| 2006/0206110 A1* | 9/2006 | Knowlton et al. ............. 606/41 |
| 2007/0010809 A1* | 1/2007 | Hovda et al. .................... 606/41 |
| 2007/0058825 A1* | 3/2007 | Suzuki et al. ................. 381/174 |
| 2007/0088413 A1* | 4/2007 | Weber et al. .................... 607/99 |
| 2008/0030122 A1* | 2/2008 | Yamage ........................ 313/495 |
| 2008/0140113 A1* | 6/2008 | Taimisto et al. ............. 606/213 |
| 2008/0200969 A1 | 8/2008 | Weber |
| 2008/0249522 A1* | 10/2008 | Pappone et al. ................. 606/41 |
| 2009/0076495 A2* | 3/2009 | Dando et al. .................... 606/34 |
| 2009/0230823 A1* | 9/2009 | Kushculey et al. ........... 310/366 |
| 2010/0004649 A1* | 1/2010 | Baker ............................. 606/33 |
| 2010/0041986 A1* | 2/2010 | Nguyen et al. ................ 600/427 |
| 2010/0262140 A1* | 10/2010 | Watson et al. .................. 606/41 |
| 2011/0137382 A1* | 6/2011 | Swanson ......................... 607/72 |
| 2011/0166559 A1* | 7/2011 | Eckhouse et al. ................ 606/9 |
| 2011/0251527 A1* | 10/2011 | Kushculey et al. .............. 601/2 |
| 2011/0301683 A1* | 12/2011 | Axelgaard .................... 607/149 |
| 2012/0107520 A1* | 5/2012 | West et al. .................... 427/534 |
| 2012/0191089 A1* | 7/2012 | Gonzalez et al. ............... 606/45 |
| 2012/0245578 A1* | 9/2012 | Van Wyk et al. ............... 606/33 |
| 2013/0079766 A1* | 3/2013 | Adanny et al. .................. 606/33 |
| 2013/0085557 A1* | 4/2013 | Terasawa ...................... 607/116 |
| 2013/0090644 A1* | 4/2013 | Williams et al. ................ 606/40 |
| 2013/0165925 A1* | 6/2013 | Mathur et al. ................... 606/41 |
| 2013/0226269 A1* | 8/2013 | Eckhouse et al. ............... 607/88 |

* cited by examiner

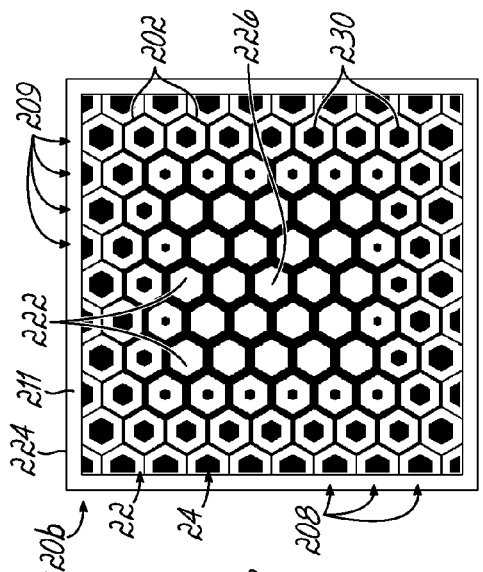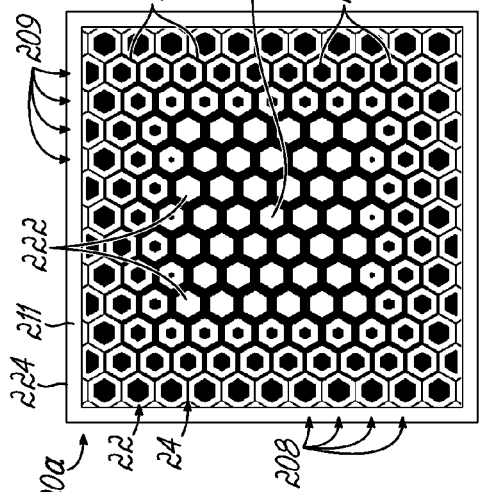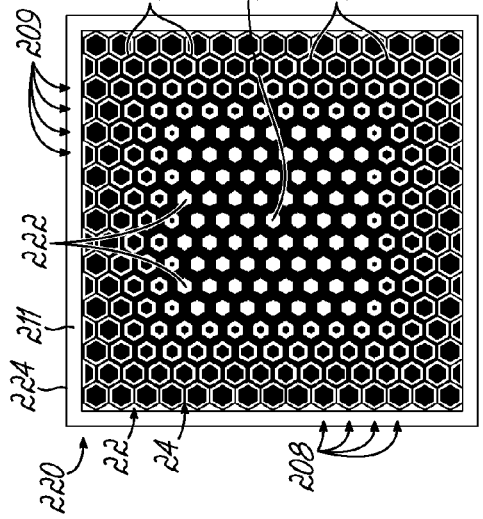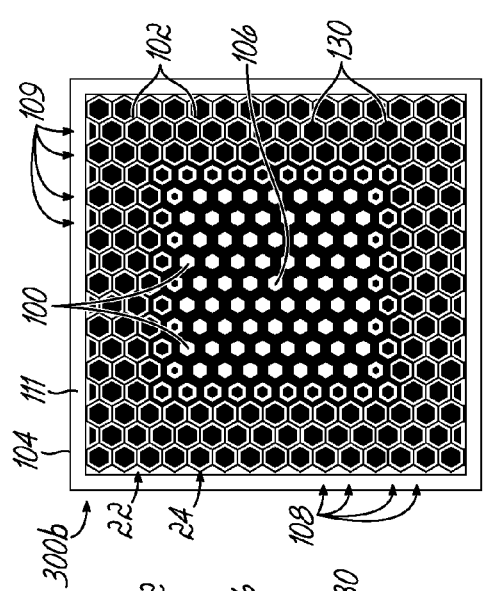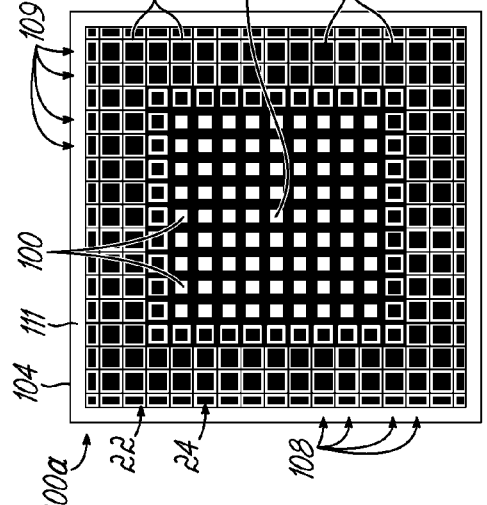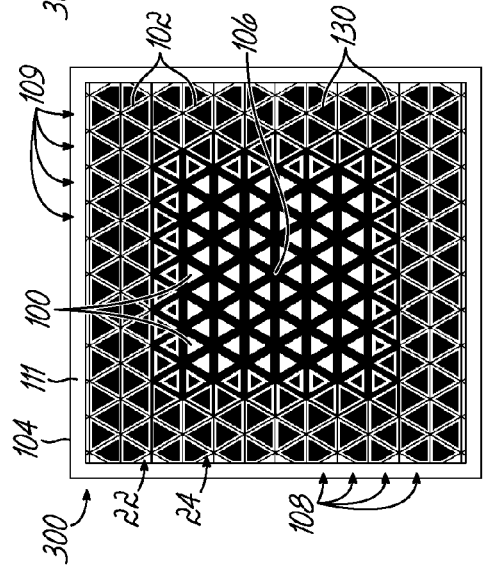

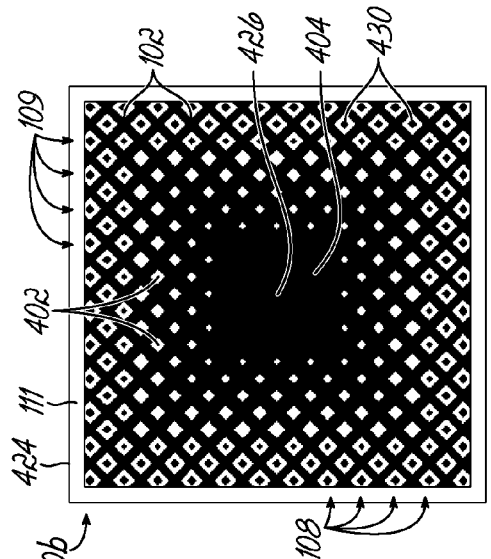
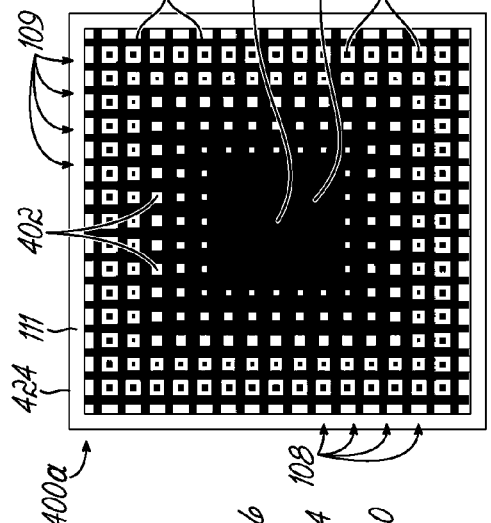
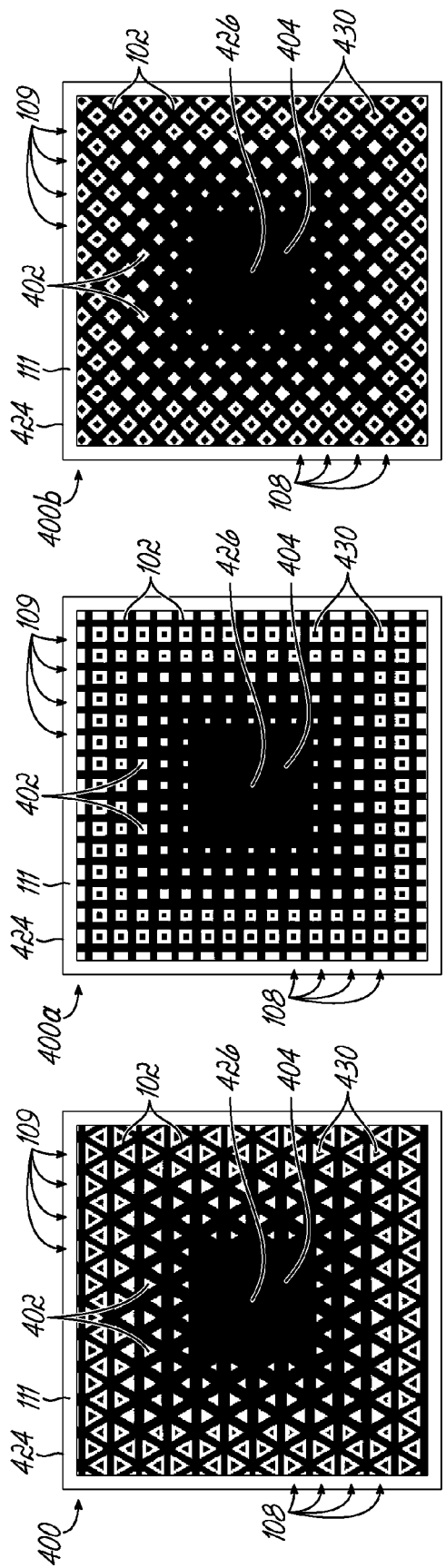
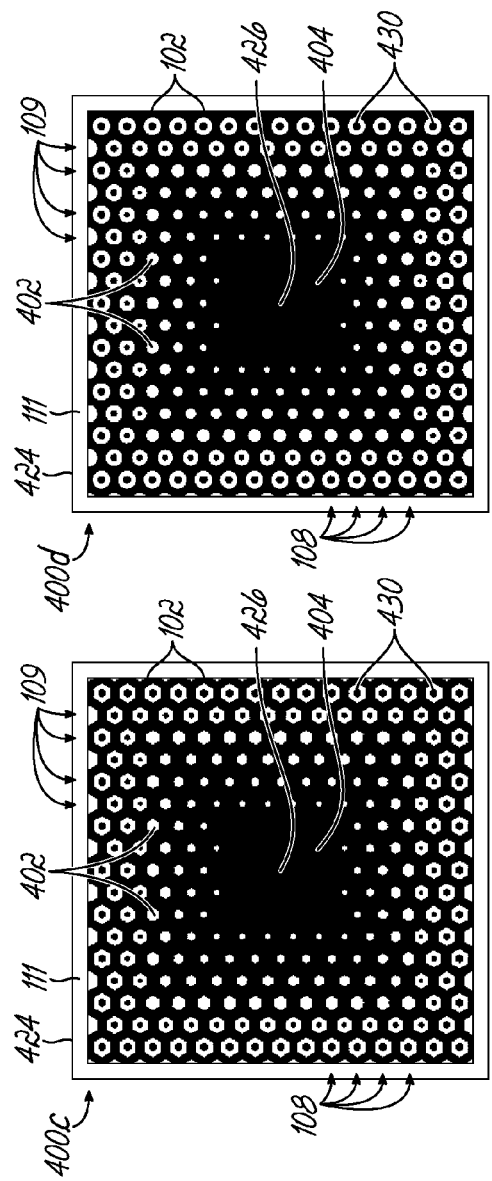
FIG. 16  FIG. 17  FIG. 18  FIG. 19  FIG. 20

PATTERNED ELECTRODES FOR TISSUE TREATMENT SYSTEMS

BACKGROUND

The invention generally relates to systems and methods for cosmetic tissue treatments and, more particularly, relates to systems and methods for treating tissue with high frequency electromagnetic energy.

Various cosmetic tissue procedures non-invasively treat tissue with high frequency electromagnetic energy in order to improve a patient's appearance. These non-invasive, procedures involve no surgery or injections, but instead deliver the high frequency electromagnetic energy through the skin surface into the tissue. High frequency electromagnetic energy applied to the different layers of the skin during a cosmetic tissue procedure can have a physiological effect on the skin's appearance.

The high frequency electromagnetic energy may be delivered from a conductor region of a treatment electrode to the tissue. The conductor region of the treatment electrode may be in contact with the tissue surface. Generally, a higher energy density of high frequency electromagnetic energy is delivered at the perimeter of the treatment electrode as an artifact of the edge at the perimeter. This edge effect produces observable results.

The transferred electromagnetic energy heats the tissue. One result of the edge effect is that the tissue heating is non-uniform across the surface area of the conductor region. Specifically, tissue proximate to the outer peripheral edge of the treatment electrode is heated to a higher temperature compared with tissue inward from the outer peripheral edge. Another result of the edge effect is that the patient may experience heat-related pain. This heat-related pain may be alleviated by reducing the treatment level. However, the reduction in treatment level to alleviate pain reduces the average energy density delivered during the treatment procedure, which lessens the effectiveness of the treatment.

What is needed, therefore, are apparatus and methods for reducing the edge effect associated with such tissue treatments so that patient discomfort is alleviated, a higher average energy density can be delivered, and therapeutic results can be improved.

SUMMARY OF THE INVENTION

The invention is generally directed to apparatus and methods that deliver electromagnetic energy to tissue at or beneath a tissue surface with an effective reduction of the edge effect and an improvement in the uniformity of the delivered electromagnetic energy. The resulting level of heating at a particular depth may be more constant. The uniform energy distribution may be useful when delivering the electromagnetic energy by stamping.

In one embodiment, an apparatus includes a treatment tip with a treatment electrode. The treatment electrode includes a conductive layer, a plurality of first openings extending through the conductive layer, and a plurality of second openings extending through the conductive layer. The first openings differ in size from the second openings.

In one embodiment, an apparatus includes a treatment tip with a treatment electrode. The treatment electrode includes a conductive layer with an outer perimeter and a plurality of openings extending through the conductive layer. The openings increasing in size with decreasing distance from the outer perimeter.

In another embodiment, a method is provided for operating a tissue treatment apparatus. The method includes contacting a dielectric layer of a treatment electrode with a tissue surface and capacitively transferring electromagnetic energy from a conductive layer of the treatment electrode through the dielectric layer to tissue beneath the tissue surface. During the capacitive transfer of electromagnetic energy, a local capacitance is dependent upon position on a surface of the conductive layer of the treatment electrode.

BRIEF DESCRIPTION OF THE DRAWINGS

FIGS. 10-12 are end views of patterned treatment electrodes in accordance with embodiments of the invention.

FIGS. 13-15 are end views of patterned treatment electrodes in accordance with embodiments of the invention.

FIGS. 16-20 are end views of patterned treatment electrodes in accordance with embodiments of the invention.

DETAILED DESCRIPTION

Figure 1:
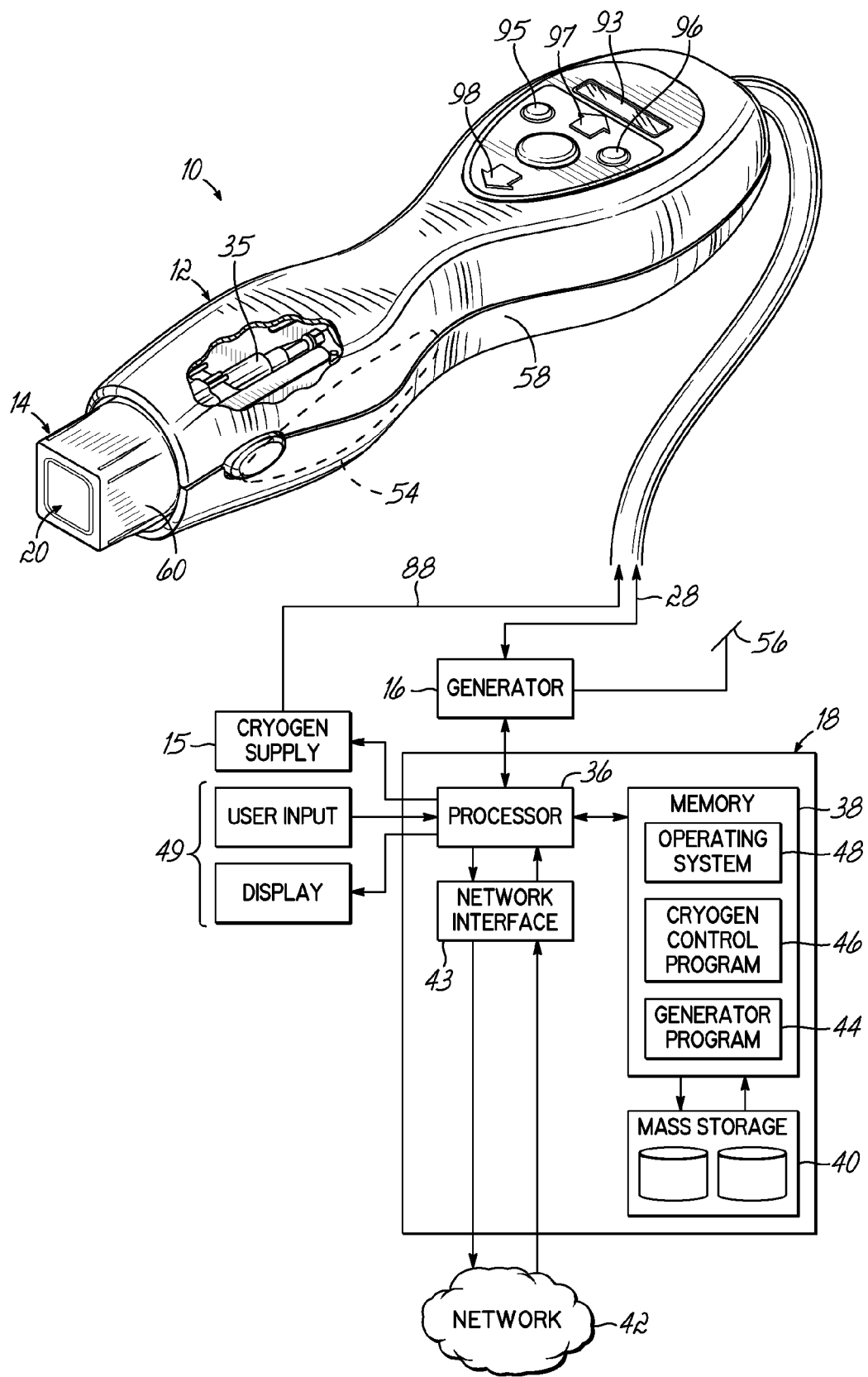
FIG. 1 is a diagrammatic view of a treatment system with a handpiece, a treatment tip, a control system, and a generator in accordance with an embodiment of the invention.
Figure 2:
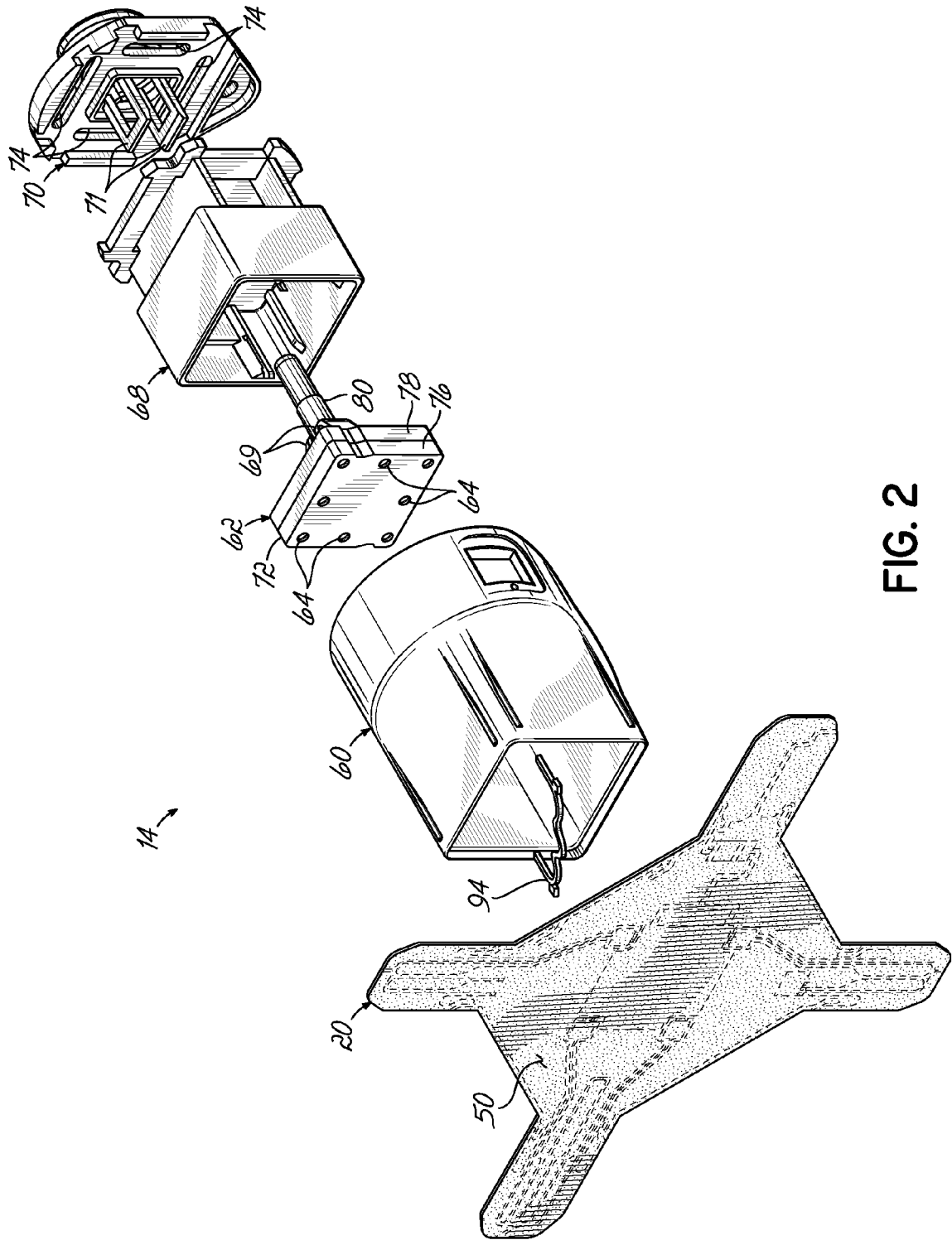
FIG. 2 is an exploded view of the treatment tip of FIG. 1.
Figure 2A:
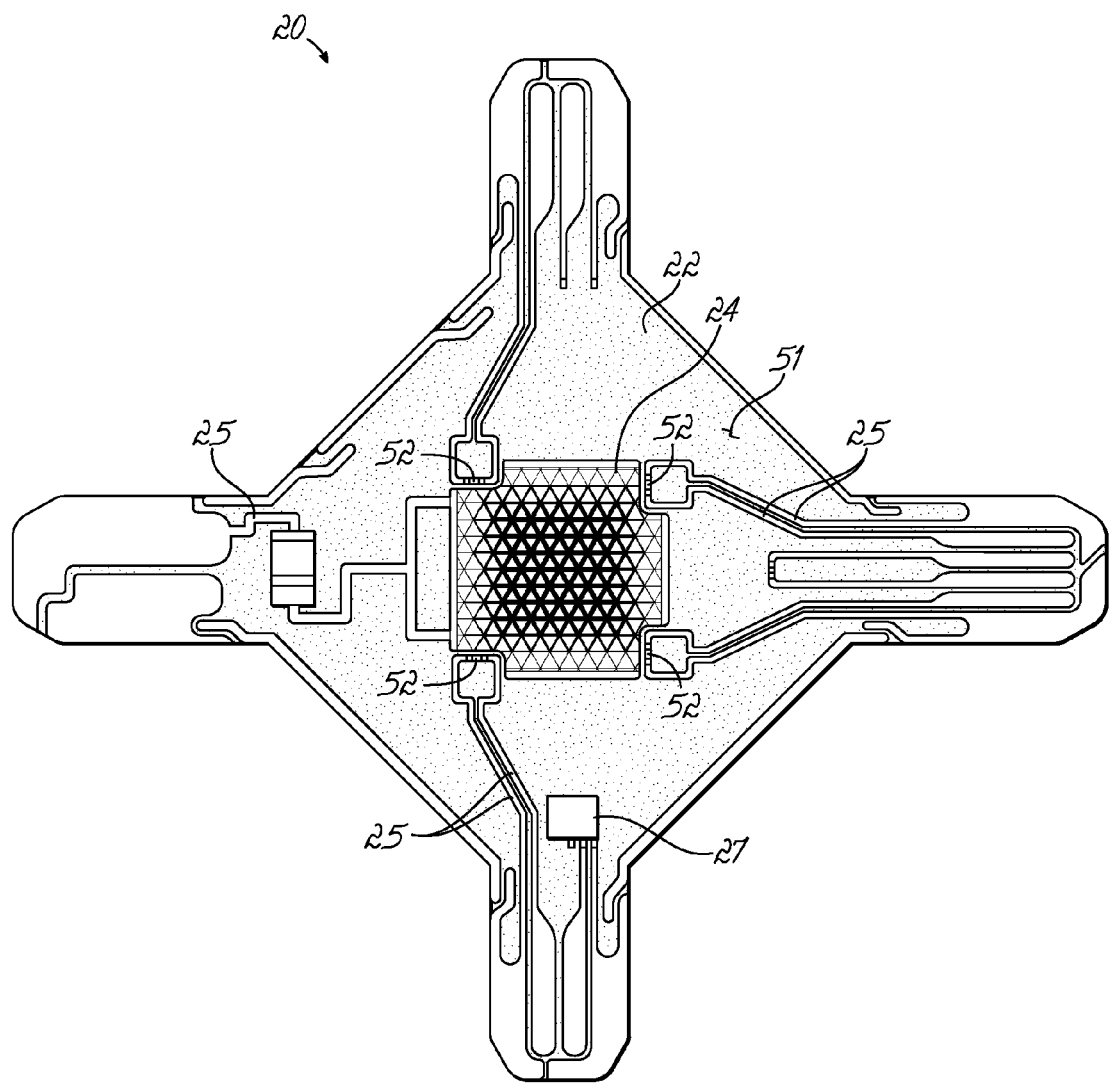
FIG. 2A is a view of the backside of the treatment electrode.

With reference to FIGS. 1, 2, 2A, and 3, a treatment apparatus 10 may include a handpiece 12, a treatment tip 14, a cryogen supply 15, a generator 16, and a system controller 18. The treatment tip 14 is coupled in a removable and releasable manner with the handpiece 12. The treatment tip 14 carries an electromagnetic energy delivery member in the representative form of a treatment electrode 20. The treatment apparatus 10 may be employed to conduct a procedure that non-invasively treats tissue beneath a tissue surface and, in certain embodiments, may be used to conduct a cosmetic procedure that non-invasively and transcutaneously treats skin tissue beneath the skin surface with electromagnetic energy in order to improve a patient's appearance.

In a representative embodiment, the treatment electrode 20 may comprise a flex circuit that includes an electrically-insulating dielectric layer 22 comprised of a non-conductive dielectric material and a conductive layer 24 comprised of a metal on and in contact with the electrically-insulating dielectric layer 22. Conductive (e.g., metal) traces or leads 25 on the dielectric layer 22 are used to electrically couple the conductive layer 24 with the generator 16. In one embodiment, the dielectric layer 22 of the treatment electrode 20 may comprise a thin flexible base polymer film carrying the conductive layer 24. The base polymer film of dielectric layer 22 may be, for example, polyimide or another material with a relatively high electrical resistivity and a relatively high thermal conductivity, and that has a constant physical thickness. The conductive layer 24 is configured to carry high-frequency current received from the generator 16 and for capacitive coupling to tissue through the dielectric layer 22.

The conductive layer 24 of the treatment electrode 20 is electrically coupled by a set of insulated and shielded conductors 28 that extend from the handpiece 12 to the generator 16. The dielectric layer 22 may also carry a non-volatile memory device 27, such as an Erasable Programmable Read-Only Memory (EPROM), that retains its held data when unpowered. The memory device 27 is coupled by the conductive leads 25 with the system controller 18.

The generator 16, which has the representative form of a high frequency power supply, is equipped with a conventional electrical circuit operative to generate high frequency electrical current, typically in the radio-frequency (RF) band of the electromagnetic spectrum. The operating frequency of generator 16 may be in the range of 200 kHz to about 50 MHz. In one embodiment, the generator 16 is a 400 watt, 6.78 MHz high frequency generator. The electrical circuit in the generator 16 converts a line alternating current voltage into drive signals for the treatment electrode 20. The drive signals are characterized by parameters (e.g., energy content and duty cycle) appropriate to provide the amount of power and the mode of operation that have been selected by the clinician.

The system controller 18 is interfaced with the cryogen supply 15 and with the generator 16, and coordinates the operation of the treatment apparatus 10. In particular, the system controller 18 regulates the power delivered from the generator 16 to the treatment electrode 20 by setting the operational parameters of the generator 16 and by setting the operational parameters of the cryogen supply 15. Under the automated control of the system controller 18 and with operator interaction with controls at the system controller 18 and handpiece 12, the treatment apparatus 10 is configured to deliver electromagnetic energy in a high frequency band of the electromagnetic spectrum, such as the radiofrequency (RF) band, to an region of a patient's tissue 30 beneath a tissue surface.

Figure 3:
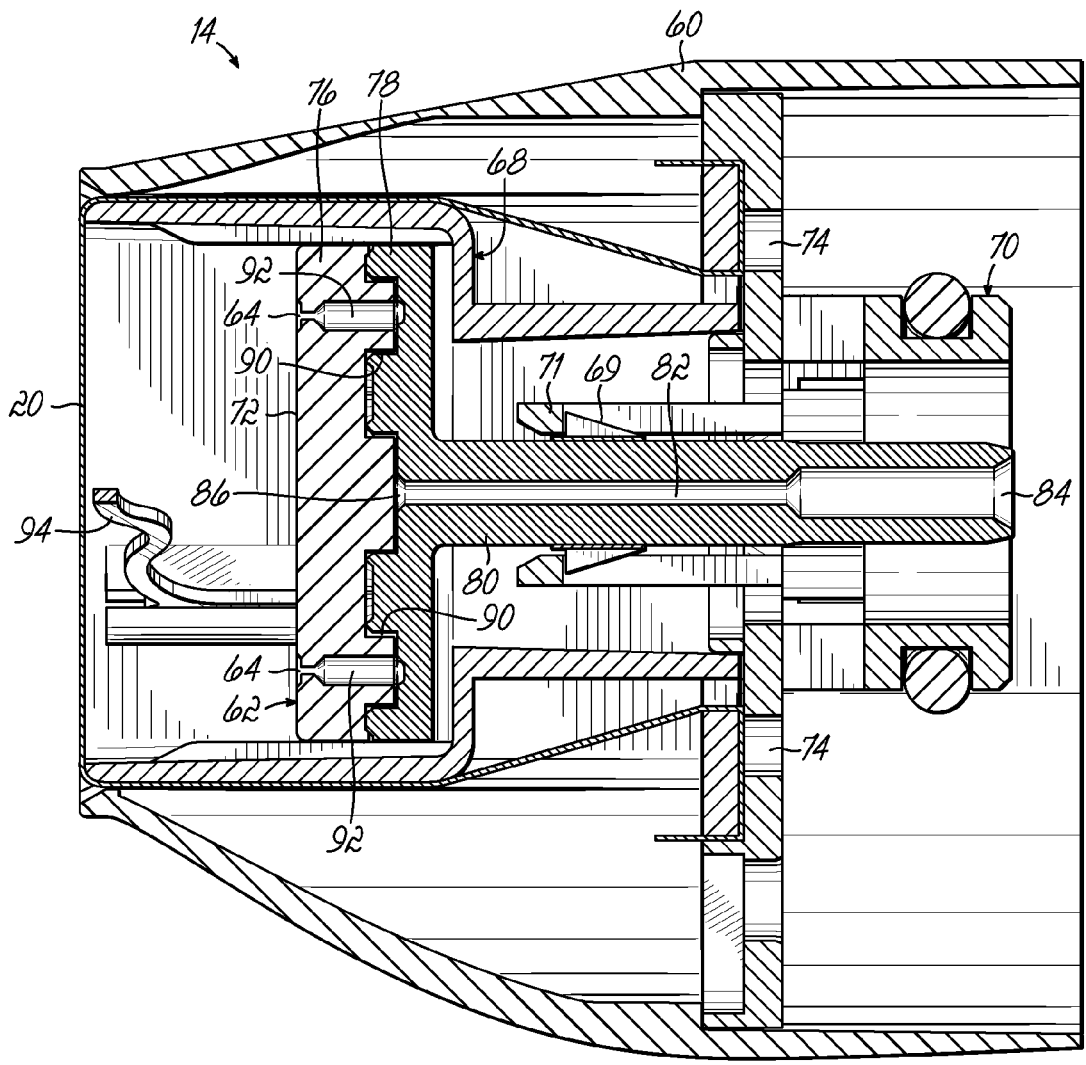
FIG. 3 is a diagrammatic cross-sectional view of the treatment tip of FIGS. 1 and 2.
Figure 3A:
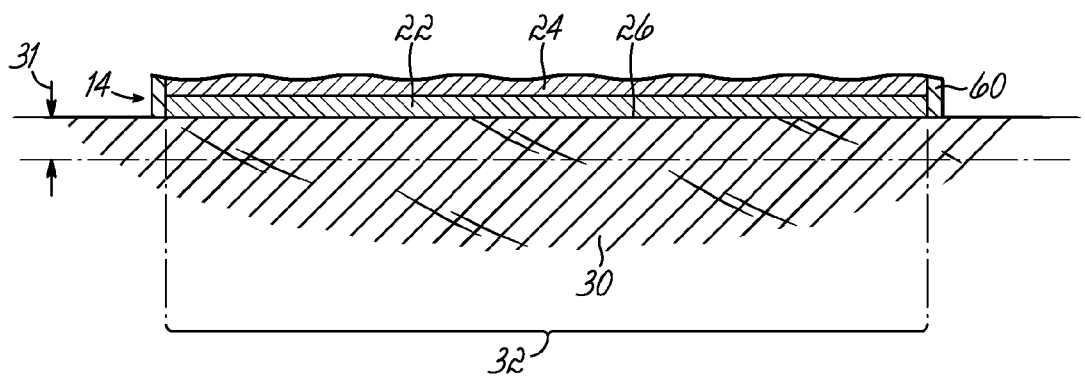
FIG. 3A is a cross-sectional view of a portion of the treatment tip in contact with the skin surface.

As best shown in FIG. 3A, the dielectric layer 22 is preferably in direct contact with the surface of the tissue, in this instance the skin surface. The electromagnetic energy volumetrically heats tissue 30 in a targeted region 32 across a targeted depth beneath the patient's skin surface 26. The heating may raise the temperature of the tissue in targeted region 32 to a therapeutic temperature or range of therapeutic temperatures. The temperature elevation within the targeted region 32 may produce for example, changes in collagen in the tissue 30 that achieve a desired treatment result, such as removing or reducing wrinkles and otherwise tightening the skin to thereby improve the appearance of a patient receiving the treatment. Because of the concurrent cooling inward from the skin surface 26, a region 31 of the tissue 30 between region 32 and the skin surface 26 may be heated to a non-therapeutic temperature such that this shallow tissue region 31 is not modified by the heating.

System controller 18 may represent practically any computer, computer system, or programmable device recognized by a person having ordinary skill in the art. System controller 18 typically includes a processor 36 coupled to a memory 38. Processor 36 may represent one or more processors (e.g., microprocessors), and memory 38 may represent the random access memory (RAM) devices comprising the main storage of system controller 18, as well as any supplemental levels of memory, e.g., cache memories, non-volatile or backup memories (e.g., programmable or flash memories), read-only memories, etc. In addition, memory 38 may be considered to include memory storage physically located elsewhere in system controller 18, e.g., any cache memory in processor 36, as well as any storage capacity used as a virtual memory, e.g., as stored on a mass storage device 40 or another computer coupled to system controller 18 via a network interface 43 over a network 42. The system controller 18 operates under the control of an operating system 48, and executes or otherwise relies upon various computer software applications, components, programs, objects, modules, data structures, etc. (e.g., power modulation control program 44 or cryogen control program 46 executing in memory 38).

The system controller 18 includes digital and/or analog circuitry that interfaces with the cryogen supply 15 and the generator 16 for supplying control signals to the cryogen supply 15 and generator 16 and receiving feedback information from sensors that is used in generating the control signals. Cryogen control program 46, which is resident as an application in the memory 38, is executed as an algorithm by the processor 36 in order to issue commands that control the operation of the cryogen supply 15. Generator control program 44, which is resident as an application in the memory 38, is executed as an algorithm by the processor 36 in order to issue commands that control the operation of the generator 16. The mass storage device 40 may store a copy of the generator control program 44 and a copy of the cryogen control program 46.

The system controller 18 also typically receives a number of inputs and outputs for external communication of information. The system controller 18 typically includes one or more user interface devices 49, such as input devices (e.g., a keyboard, a mouse, a trackball, a joystick, a touchpad, a keypad, a stylus, and/or a microphone, among others), that provide a user or operator interface. Interface devices 49 may also include a display or other output device (e.g., a CRT monitor, an LCD display panel, and/or a speaker, among others). The interface to the system controller 18 may also be through an external terminal connected directly or remotely to system controller 18, or through another single (or multi) user computer (not shown) communicating with the system controller 18 via network 42, modem, or other type of communications device. Instructions delivered to the system controller 18 via the user interface devices 49 may be used to adjust the generator 16 to establish an arbitrary treatment setting. Information displayed by the user interface devices 49 may include the amount of energy delivered, tissue impedance, duration, and feedback to the operator relating to procedure technique. System controller 18 may optionally be linked with a non-volatile memory (not shown) carried by the handpiece 12 or with a nonvolatile memory (not shown) carried by the treatment tip 14.

During tissue treatment, a surface 50 of the dielectric layer 22 of treatment electrode 20 is placed into a directly contacting relationship with the skin surface 26 of the patient. The conductive layer 24 of the treatment electrode 20 is physically carried on a non-contact side or surface 51 of the dielectric layer 22 of the treatment electrode 20 and is therefore separated by the dielectric layer 22 from the skin surface 26 (FIG. 3A). Hence, in the representative embodiment, the dielectric layer 22 is arranged between the conductive layer 24 and the skin surface 26. Electromagnetic energy is transmitted in a transcutaneous manner from the conductive layer 24 on one side 51 of the dielectric layer 22 through the thickness of dielectric layer 22 across the area of the surface 50 registered with the conductive layer 24 to the corresponding surface area of skin surface 26 and the underlying tissue 30 by capacitively coupling with the tissue 30.

The treatment tip 14 includes a plurality of sensors 52 that output readings that are used as feedback by the system controller 18 to control the treatment process. Conductive leads 25 on the dielectric layer 22 are used to electrically couple the sensors 52 with the system controller 18. In one embodiment, the sensors are temperature sensors 52, such as thermistors or thermocouples, that are constructed to detect the temperature of the treatment electrode 20 and/or treatment tip 14. In the representative embodiment, the temperature sensors 52 are disposed on the surface 51. The measured temperature reflects the temperature of the treated tissue 30 and may be used as feedback in a control loop by the system controller 18 for controlling energy delivery and/or cooling of the skin surface 26. The handpiece 12 or treatment tip 14 may also include pressure sensors (not shown) for detecting physical contact between the treatment electrode 20 and the skin surface 26. In an alternative embodiment, one or more of the sensors 52 may be impedance sensors.

An activation button 54, which is accessible to the operator from the exterior of the handpiece 12, is configured to be actuated to close a switch in a normally open circuit with the generator 16. The closed circuit energizes the treatment electrode 20. Actuation of the activation button 54 triggers delivery of a dose of the high frequency energy over a short timed delivery cycle to the target tissue 30. After a lapsed treatment time, the delivery of high frequency energy from the treatment electrode 20 to the tissue 30 at the treatment site is discontinued and the handpiece 12 is manipulated to position the treatment tip 14 near a different treatment site on the skin surface 26. Another cycle is then initiated to deliver another dose of high frequency energy to the patient's tissue 30. The treat and move process is repeated for an arbitrary number of treatment sites distributed across the skin surface 26.

High frequency electrical current flowing between the treatment electrode 20 and the patient is concentrated at the skin surface 26 and within the underlying tissue 30 across the contacting surface area of the treatment electrode 20. Capacitive coupling of the high frequency electromagnetic energy relies on energy transfer through the dielectric material of the dielectric layer 22 to create an electric field across the surface area where the treatment electrode 20 contacts the patient's body. The time-varying electric field induces electrical currents within the surrounding tissue 30 beneath the skin surface 26. Because of the natural resistance of tissue 30 to electrical current flow, volumetric heating results within the tissue 30. The volumetric heating delivers a therapeutic effect to the region 32 of the tissue 30 near the treatment site. For example, heating to a temperature of 60° C. or higher may contract collagen fibers and/or form nascent collagen within the region 32, which will result in tissue tightening or another aesthetic effect to improve the patient's appearance. The heating depth in the tissue 30 is based upon the size and geometry of the treatment electrode 20 and, contingent upon the selection and configuration of the treatment tip 14 and cooling with a reverse thermal gradient, can be controlled to extend from a few hundred microns beneath the skin surface 26 to several millimeters.

A non-therapeutic passive return electrode 56 is used to electrically couple the patient with the generator 16. During patient treatment, the high frequency current flows from the treatment electrode 20 through the treated tissue 30 and the intervening bulk of the patient to the return electrode 56 and then to the generator 16 through the shielded conductors 28 to define a closed circuit or current path. The return electrode 56 is physically attached by, for example, adhesive to a site on the body surface of the patient, such as the patient's back. The surface area of the return electrode 56 in contact with the patient is relatively large in comparison with the surface area of the treatment electrode 20. Consequently, at the tissue adjacent to the return electrode 56, the current density flowing from the patient to the return electrode 56 is distributed across the larger surface area and is relatively low in comparison with the current density flowing from the treatment electrode 20 of smaller surface area to the patient. Because negligible heating is produced at its attachment site to the patient, a non-therapeutic effect is created in the tissue adjacent to the return electrode 56.

With continued reference to FIGS. 1, 2, 2A, and 3, the handpiece 12 includes an outer housing 58 and the treatment tip 14 includes an outer housing 60 that is mechanically coupled with the housing 58 to establish an assembly. The handpiece 12 and treatment tip 14 include complementary electrical/fluid interfaces (not shown) that are coupled together when the housings 58, 60 are mechanically coupled. The housings 58, 60 may be fabricated by an injection molding process using a suitable polymer resin as a construction material. The outer housing 58 of handpiece 12 has a smoothly contoured shape suitable for gripping and manipulation by an operator. The operator maneuvers the treatment tip 14 and treatment electrode 20 to a location proximate to the skin surface 26 and, typically, a location that places the treatment electrode 20 in a contacting relationship with the skin surface 26.

The treatment tip 14 includes the treatment electrode 20, the housing 60, a nozzle 62 that is configured with a head 72 having multiple orifices 64, and a pair of structural members 68, 70 that support the nozzle 62. The structural member 68, 70 are assembled with the nozzle 62 such that the head 72 of the nozzle 62 is recessed inside the similarly shaped hollow interior of the structural member 68. The assembly of the treatment electrode 20 and structural members 68, 70 is secured together by complementary clip fasteners 69, 71 on the nozzle 62 and structural member 70. The treatment electrode 20, which is shown in an unfolded state, is wrapped about the exterior of the structural member 68 such that the leads 25 can be contacted through openings 74 defined in structural member 70. A bridge 94 provides backside mechanical support and rigidity to the flexible treatment electrode 20. An optional heat spreader (not shown) may be disposed between the head 72 and the treatment electrode 20.

The nozzle 62 is an assembly that includes a spray plate 76, a flange 78 that is coupled with the spray plate 76 to define the head 72, and a stem 80 that extends rearwardly from the flange 78. Extending axially along the length of the stem 80 is a flow channel 82 with an inlet 84 and an outlet 86. Cryogen is pumped from the cryogen supply 15 through tubing 88 partially inside the handpiece 12 and mechanically coupled with the inlet 84 to the flow channel 82. The cryogen supply 15 may be a pre-filled canister containing a pressurized cryogen, such as a low boiling point fluid like 1,1-Difluoroethane (R-152a refrigerant) or 1,1,1,2-Tetrafluoroethane (R-134a refrigerant). Disposed between the flange 78 and spray plate 76 is a system of flow channels 90 that distributed the cryogen to passages 92 extending through the thickness of the spray plate 76. Each of the passages 92 terminates at one of the orifices 64.

The cryogen is ejected in a pulse as an atomized or non-atomized stream of coolant from each of the orifices 64 toward the surface 51 of the treatment electrode 20 and, in particular, toward the conductive layer 24. The cryogen impinges and wets the surface 51 of the treatment electrode 20 and subsequently evaporates, which extracts heat and produces the cooling. Because of the low thermal mass, the temperature of the treatment electrode 20 drops rapidly upon evaporation. The cooling effect from the reduced temperature is communicated through the dielectric layer 22 to the skin surface 26 and into the tissue 30 to extract heat from the tissue 30. The cooling competes with the volumetric heating from the high frequency energy such that a reverse thermal gradient is produced in tissue 30 and the therapeutic effect is delivered only to the region 32. The cooling of the reverse thermal gradient protects the region of tissue 30 between region 32 and the skin surface 26 from reaching a therapeutic temperature. The cooling is superimposed on the heating profile such that the skin surface 26 is cooler than the region 32 and the temperature increases in a temperature gradient from the skin surface 26 to the region 32.

The handpiece 12 is equipped with a valve 35 used to deliver a metered amount of cryogen, as a spray, a stream, or another physical form, to the treatment electrode 20. In the representative embodiment, the metered amounts of cryogen are expelled or discharged from the nozzle 62 as cryogen pulses directed toward the surface 51 of the treatment electrode 20 and, in particular, toward the conductive layer 24 of treatment electrode 20. Various duty cycles of cooling and heating that rely on cooling and high frequency energy transfer from the treatment electrode 20 are utilized contingent upon the type of treatment and the desired type of therapeutic effect. The cooling and heating duty cycles may be controlled and coordinated by operation of the system controller 18.

The patient's epidermis may be cooled by a cryogen spray in order to prevent harm to the epidermis. The cryogen spray is preferably used to pre-cool the patient's epidermis, before powering the treatment electrode 20, by heat transfer between the treatment electrode 20 and the epidermis. The cooling creates a reverse thermal gradient in the tissue 30 such that the temperature of the tissue 30 at the skin surface 26 is cooler than the temperature of the tissue 30 within the epidermis or dermis. As a result, the high frequency energy delivered to the tissue 30 fails to heat all or a portion of the patient's epidermis to a temperature sufficient to cause significant epidermal thermal damage. The region 32 of tissue 30 that is not significantly cooled by pre-cooling will volumetrically warm up to therapeutic temperatures, which cause a desired therapeutic effect. The amount and/or duration of pre-cooling may be used to select the protected depth of untreated tissue 30 between the region 32 and the skin surface 26. The metered delivery of cryogen by the valve 35 to the treatment tip 14 may also be used to cool portions of the tissue 30 during and/or after heating by the high frequency energy transferred from the treatment electrode 20. Post-cooling may prevent or reduce heat delivered deeper into the region 32 of the tissue 30 from conducting upward and heating shallower tissue regions, such as the epidermis, to temperatures which could thermally damage the epidermis even though external energy delivery to the targeted tissue 30 has ceased.

The handpiece 12 includes a display 93, controls 95, 96 that scroll different functions on the display 93, controls 97, 98 used to respectively increase and reduce the setting for the function currently on the display 93, and a control to engage a changed setting. The display 93 may be used to display information including, but not limited to, energy delivered, tissue impedance, duration, and feedback on procedure technique. The availability of the information displayed on the display 93 may conveniently eliminate the need to display identical information on the interface devices 49, or may duplicate displayed information by the interface devices 49. By displaying information at the handpiece 12, the operator can focus on the procedure without diverting his attention to glance at information displayed by the display on the interface devices 49. In one embodiment, the display 93 may constitute a thin, flat liquid crystal display (LCD) comprised of a light source or reflector and an arbitrary number of color or monochrome pixels arrayed in front of the light source or reflector. A driver circuit (not shown) is provided to control the operation of the display 93.

Figure 4:
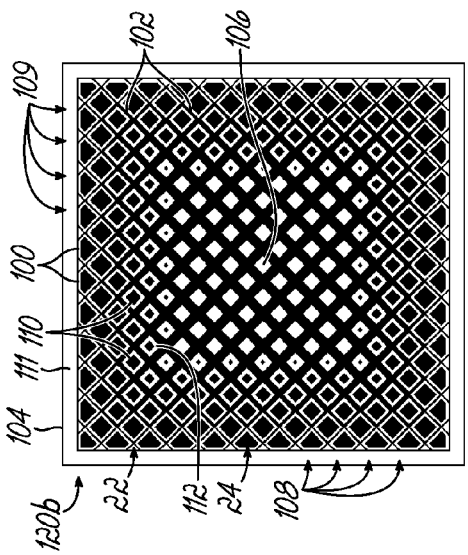
FIG. 4 is an end view of a patterned treatment electrode in accordance with an embodiment of the invention.

With reference to FIG. 4 in which like reference numerals refer to like features in FIGS. 1, 2, 2A, and 3 and in accordance with an embodiment of the invention, the treatment electrode 20 is configured in a manner believed to be effective for reducing the edge effect associated with such tissue treatments. Specifically, the conductive layer 24 comprises a plurality of open cells or openings 100 that are arranged in a pattern such that the conductive layer 24 is not solid. Each of the openings 100 may be a perforation or hole that penetrates from one side of the conductive layer 24 through the thickness of the conductive layer 24 to its opposite side so that the conductive layer 24 is completely removed inside the inner edge of each opening 100. In the representative embodiment, a portion of the dielectric layer 22 is exposed or revealed inside each opening 100. Each exposed portion of the dielectric layer 22 has the same shape and size as the corresponding opening. The openings 100 may be formed in the conductive layer 24 by patterning a solid layer of the constituent conductor with a conventional masking and etching process.

The conductive layer 24 is comprised of conductive paths 102 of electrical conductor and a frame 111 that is arranged about the periphery of the conductive paths 102. In the representative embodiment and because at least in part of the shape of the particular openings 100, the conductive paths 102 comprise a network of lines that intersect each other in a grid and that have ends coupled with the frame 111. Either the inner edge or the outer edge of the frame 111 may be considered to constitute an outer perimeter 104 of the treatment electrode 20. The treatment electrode 20 also includes a geometrical center 106 that is surrounded by the outer perimeter 104 and frame 111. The geometrical center 106 may be used as a point of reference for determining the relative positions of the openings 100. The frame 111 is used to connect the conductive paths 102 with the generator 16 for powering the treatment electrode 20 during use.

Each of the openings 100 has a geometrical shape and, in the representative embodiment, the openings 100 are shaped as open triangles. However, the openings 100 may alternatively have a different geometrical shape, such as circles or regular polygons like open rectangles for a treatment electrode 20a (FIG. 5), open diamonds of a different angular orientation for a treatment electrode 20b (FIG. 6), or others (e.g., open hexagons as depicted in FIGS. 10-12, 15). All of the openings 100 preferably have nominally the same geometrical shape. The openings 100 may have a uniform placement with respect to a center-to-center separation or pitch across the surface area of the treatment electrode 20.

The local capacitance to the tissue may be modulated across the surface area of the treatment electrode 20 by varying the dimensions (i.e., size and/or area) of the openings 100. In the representative embodiment, the area of the openings 100 is largest near the outer perimeter 104 and smallest near the geometrical center 106. The openings 100 may be generally considered to be arranged, for example, in rows 108 or in rows 109 along which the opening size varies and, in the representative embodiment, generally becomes larger (i.e., grow in size) in a direction from the geometrical center 106 toward the outer perimeter 104. The dimensional modulation may be provided by locally varying a line width of each conductive path 102. In the representative embodiment, the line width is selected such that the openings 100 have a constant size over a central area, and increase in size with decreasing separation or distance from the outer perimeter 104.

As a result of the position dependence of the opening size, the exposed area of dielectric layer 22 inside each opening 100 is greater near the outer perimeter 104 of treatment electrode 20 than near its geometrical center 106. Conversely, because of the position dependence of the opening size, the fraction of the surface area covered by the conductive material of the conductive layer 24 is greater near the geometrical center 106 than near the outer perimeter 104. In other words, the amount of conductor per unit area of the conductive layer 24 decreases with decreasing distance from the outer perimeter 104.

The capacitance of the treatment electrode 20 may be controlled during electrode design by selecting the total open area of openings 100 and the exposed area of the dielectric layer 22, as well as other factors such as the permittivity and thickness of the dielectric layer 22. The local capacitance to the tissue and the local heating under the treatment electrode 20 have a position dependence and, in particular, decrease with decreasing distance from the outer perimeter 104 as the opening size increases. The decrease in the local heating near the outer perimeter 104 operates to offset and reduce the edge heating effect observed at the outer edge of conventional electrodes. Varying the size of the openings 100 allows the heating profile of the electrode to be precisely adjusted so that more uniform heating of tissue beneath the electrode during a patient treatment will result as compared to conventional electrodes.

Figure 5:
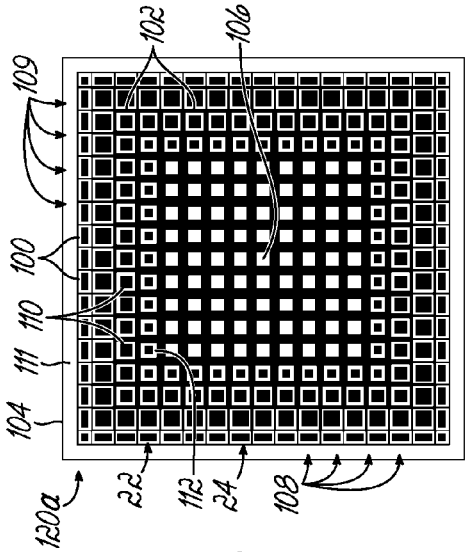
FIGS. 5 and 6 are end views similar to FIG. 4 of patterned treatment electrodes in accordance with other embodiments of the invention.
Figure 6:
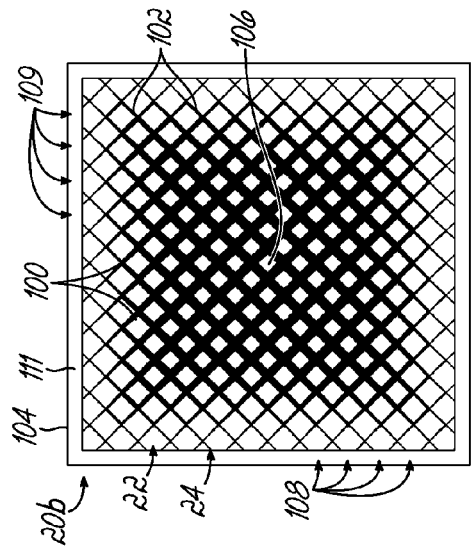
Figure 7:
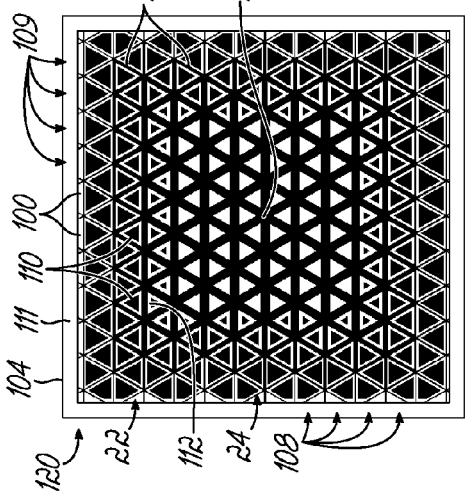
FIG. 7 is an end view of a patterned treatment electrode in accordance with an embodiment of the invention.

With reference to FIG. 7 in which like reference numerals refer to like features in FIGS. 4-6 and in accordance with an embodiment of the invention, a treatment electrode 120 further includes discrete conductive patches or islands 110 that partially occupy or fill some or all of openings 100 of treatment electrode 20. The conductive material comprising the islands 110 may be the same conductive material as constituting the conductive paths 102 and the islands 110 may be concurrently formed along with the conductive paths 102 using the same fabrication processes. However, the islands 110 are not electrically continuous with the conductive paths 102. Instead, the islands 110 are electrically isolated from the conductive paths 102 by respective gaps 112 in the conductive layer 24 so that the dielectric material of the dielectric layer 22 provides electrical isolation. Because the islands 110 are electrically floating, the amount of conductor per unit area of the conductive layer 24 coupled with the generator 16 also decreases with decreasing distance from the outer perimeter 104 similar to treatment electrode 20.

The islands 110 may be positioned inside the openings such that the gaps 112 have a uniform width around the circumference of the islands 110. In one embodiment, each island 110 is centered inside its corresponding opening 100. The fill shape of the islands 110 may be the complement of the geometrical shape of the openings 100. In the representative embodiment, the fill shape of each island 110 is a solid triangle to match the open triangle geometrical shape of the corresponding opening 100. However, the islands 110 may alternatively have a different closed fill shape, such as solid rectangles for treatment electrode 120a (FIG. 8), solid diamonds for treatment electrode 120b (FIG. 9), or any other geometrical shape (e.g., solid hexagons), and the openings 100 may have the complementary shape (e.g., open rectangles) but of larger dimensions than the islands 110. The shape correspondence and dimensional differences create the gap 112 between the outer edge(s) of each island 110 and the inner edge(s) of the conductive layer 24 about the corresponding opening 100. In the representative embodiment, all of the islands 110 have nominally the same geometrical shape.

In the representative embodiment, openings 100 near the center of the treatment electrode 20 are not occupied (i.e., are not partially filled) by the islands 110. At a specific distance from the geometrical center 106, the islands 110 are provided in openings 100 to supply the partial filling. Generally, the size of the islands 110 increases as distance from the outer perimeter 104 decreases. In one embodiment, the size of the individual islands 110 and openings 100 is correlated such that the area of exposed material of dielectric layer 22 in the gaps 112 is constant for all of the openings 100. The commensurate change in opening size and fill shape size may operate to reduce variation of surface cooling through the treatment electrode 20. Heat transfer through multiple layers (dielectric layer 22 and conductive layer 24) is different than heat transfer exclusively through the dielectric layer 22. Hence, a constant ratio of conductor surface to exposed dielectric surface may improve temperature uniformity across the treatment electrode 20, but only nominally impact the reduction in the edge effect because the islands 110 are electrically floating With reference to FIG. 10 in which like reference numerals refer to like features in FIGS. 4-9 and in accordance with an embodiment of the invention, a treatment electrode 220 includes cells or openings 222 that vary in size dependent on the location relative to a geometrical center 226. The conductive layer 24 is comprised of conductive paths 202 of electrical conductor and a frame 211 that is arranged about the periphery of the conductive paths 202. The conductive paths 202 have ends coupled with the frame 211, which is used to connect the conductive paths 202 with the generator 16 for powering the treatment electrode 20 during use. Either the inner edge or the outer edge of the frame 211 may be considered to constitute an outer perimeter 224 of the treatment electrode 200.

The size of the openings 222 is constant across an interior area of the conductive layer 24 that is a fraction of the total surface area of treatment electrode 200. However, as the outer perimeter 224 is approached, the openings 222 progressive increase in dimensions or size so that the largest of the openings 222 are proximate to the outer perimeter 224. The size variation of the openings 222 may be employed to modulate a local capacitance to the tissue across the surface area of the treatment electrode 20. The openings 100 may be generally considered to be arranged, for example, in rows 208 and in rows 209 along which the opening size varies and, in the representative embodiment, generally becomes larger (i.e., grow in size) in a direction from the geometrical center 226 toward the outer perimeter 224. In the representative embodiment, the openings 222 have a constant size over a central area, and increase in size with decreasing separation or distance from the outer perimeter 224. The openings 222 have a plurality of different sizes and, in the representative embodiment, more than two different sizes. The size of the openings 222 may be enlarged, as depicted for treatment electrode 220a (FIG. 11) having openings 222 larger than treatment electrode 220 (FIG. 10) and treatment electrode 220b (FIG. 12) having openings 222 larger than treatment electrode 220a, to vary the size distribution, average size, smallest size, largest size, etc.

Figure 8:
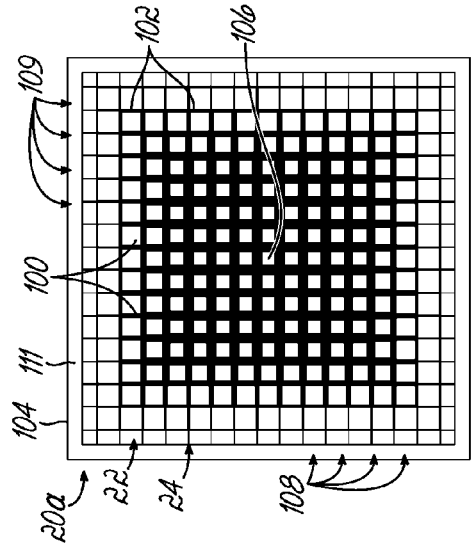
FIGS. 8 and 9 are end views similar to FIG. 7 of patterned treatment electrodes in accordance with other embodiments of the invention.
Figure 9:
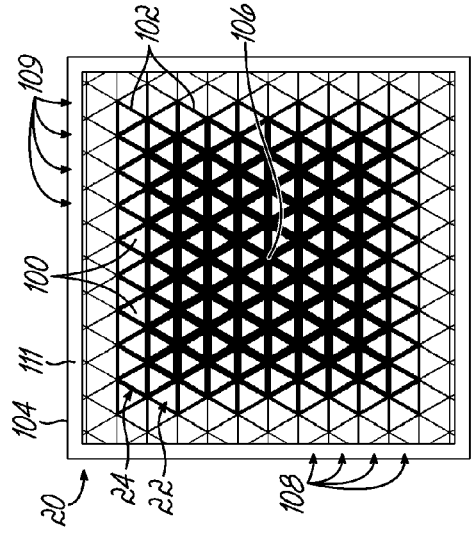

Openings 222 near the outer perimeter 224 of treatment electrode 200 may be partially filled by discrete conductive patches or islands 230 similar to islands 110 (FIGS. 7-9). The islands 230 may likewise increase in size to maintain a constant ratio of conductor surface to exposed dielectric surface, as discussed above. In the representative embodiment, the geometrical shape of each opening 222 is hexagonal and the fill shape of each island 230 is commensurately a solid hexagon to match the open hexagon geometrical shape of the corresponding opening 222. In alternative embodiments, the openings 222 and islands 230 may respectively have different geometrical shapes and fill shapes, such as diamonds or squares. In one embodiment, the size of the individual islands 230 is chosen such that the area of exposed material of dielectric layer 22 in the island-opening gaps is constant for all of the openings 222. The sizes of the openings 222 and islands 230 may be systematically varied (i.e., increased as the distance from the outer perimeter 224 decreases) to maintain the constant exposed area of dielectric layer 22.

With reference to FIG. 13 in which like reference numerals refer to like features in FIGS. 4-12 and in accordance with an embodiment of the invention, the openings 100 of a treatment electrode 300, which is otherwise similar to treatment electrode 120a (FIG. 7), have a different position-dependent size variation than treatment electrode 120a. The openings 100 of treatment electrode 300 transition more quickly (i.e., at a faster rate) from the smallest openings 100 near the geometrical center 106 to the largest openings 100 near the outer perimeter 104. Instead of transitioning over three rows 108 or three rows 109 as for treatment electrode 120a, the size transition for treatment electrode 300 occurs over two rows 108 or two rows 109. The openings 100 and islands 110 are depicted as open and solid triangles, respectively, but may alternatively have different geometrical shapes and fill shapes, such as open and solid rectangles for treatment electrode 320a (FIG. 14), open and solid hexagons for treatment electrode 320b (FIG. 15), or any other set of geometrical and fill shapes. The faster size transitioning for treatment electrode 300a is apparent from a comparison of FIG. 14 with FIG. 8, and the size transition at a higher rate for treatment electrode 300b is apparent from a comparison of FIG. 15 with FIG. 9.

With reference to FIG. 16 in which like reference numerals refer to like features in FIG. 4 and in accordance with an embodiment of the invention, a treatment electrode 400 includes cells or openings 402 that vary in size dependent on the location relative to a geometrical center 426 and a central solid region 404 that may be centered on the geometrical center 426. Openings 402 that are closest to an outer perimeter 424 may be partially filled by conductive patches or islands 430 similar to islands 110 (FIGS. 7-9) and openings 402 may be unfilled between the partially filled openings 402 and the central solid region 404. The openings 402 and islands 430 are depicted as triangular and triangles, respectively, but may alternatively have different geometrical shapes and fill shapes, such as open and solid rectangles for treatment electrode 420a (FIG. 17), open and solid diamonds for treatment electrode 420b (FIG. 18), open and solid hexagons for treatment electrode 420c (FIG. 19), open and solid circles for treatment electrode 420d (FIG. 20), or any other set of geometrical and fill shapes. The presence of the central solid region 404 may improve cooling uniformity because of the additional conductor in comparison with a treatment electrode lacking such a central solid region.

In use to perform a treatment procedure, the physician selects a type of treatment tip 14 based on the procedure to be performed and the size of the surface area on the patient to be treated, as well as the depth of cooling and heating desired for the treatment procedure. After choosing the treatment tip 14 and attaching it to the handpiece 12, the physician marks the intended treatment area on the patient with a grid of removable markings that are easily wiped away post-procedure. Each discrete square in the grid corresponds approximately to the size of the treatment electrode 20 that is placed in direct contact with the skin surface 26. The markings operate as a placement guide on the patient's skin surface 26 for the treatment procedure. The return electrode 56 is attached to the patient to supply the current path for the high frequency current back to the generator 16.

After the optional application of a conductive fluid, each square within the grid may be sequentially treated with high frequency energy delivered from the treatment electrode 20 in a stamping operation. Specifically, at each grid square, the physician lands the treatment electrode 20 directly against the patient's skin and actuates the activation button 54 on the handpiece 12. The treatment electrode 20 transmits high frequency energy to the tissue 30 beneath the skin surface 26 while serving as a contact cooling membrane for the cryogen. Information about skin temperature and contact, treatment force or pressure against the skin, cooling system function, and other types of relevant data, such as impedance may be supplied from the treatment tip 14 to the system controller 18 to precisely and safely control the high frequency energy and coolant delivery to each treatment site in the grid. Cooling the epidermis limits the temperature to lessen the likelihood of thermal damage to the epidermis. While maintaining contact with the skin surface 26 during each repetition, power and cryogen are delivered.

After energy delivery is completed during each repetition, the handpiece 12 is maneuvered to lift the treatment electrode 20 from the skin surface 26. The handpiece 12 and treatment tip 14 are moved among subsequent treatment locations in the grid and energy is delivered in a similar manner for treating large regions on the patient, such as the patient's face. Multiple passes over the entire grid of the treatment zone, separated in time by a quiescent period of a few minutes, may be used to enhance the treatment, as is understood by persons skilled in the art. Multiple treatments, which are separated temporally by a lengthier healing period, may be needed for a successful treatment that supplies the desired cosmetic effect.

References herein to terms such as "vertical", "horizontal", etc. are made by way of example, and not by way of limitation, to establish a frame of reference. It is understood that various other frames of reference may be employed for describing the invention without departing from the spirit and scope of the invention. It is also understood that features of the invention are not necessarily shown to scale in the drawings. Furthermore, to the extent that the terms "composed of", "includes", "having", "has", "with", or variants thereof are used in either the detailed description or the claims, such terms are intended to be inclusive and open-ended in a manner similar to the term "comprising."

It will be understood that when an element is described as being "attached", "connected", or "coupled" to another element, it can be directly connected or coupled to the other element or intervening elements may be present. In contrast, when an element is described as being "directly attached", "directly connected", or "directly coupled" to another element, there are no intervening elements present.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

While the invention has been illustrated by a description of various embodiments and while these embodiments have been described in considerable detail, it is not the intention of the Applicant to restrict or in any way limit the scope of the appended claims to such detail. Additional advantages and modifications will readily appear to those skilled in the art. Thus, the invention in its broader aspects is therefore not limited to the specific details, representative apparatus and method, and illustrative example shown and described. Accordingly, departures may be made from such details without departing from the spirit or scope of Applicant's general inventive concept.

What is claimed is:

1. A treatment apparatus comprising:
    a treatment tip including a treatment electrode and a dielectric layer, the treatment electrode comprising a conductive layer with an outer perimeter, a plurality of first openings extending through the conductive layer, and a plurality of second openings extending through the conductive layer, and the first openings being smaller in size than the second openings, wherein the second openings are located between the outer perimeter and the first openings, and wherein the second openings increase in size closer to the outer perimeter, wherein the conductive layer is in contact with the dielectric layer, and the conductive layer includes a conductive island inside at least some of the second openings, with the conductive islands increasing in size closer to the outer perimeter such that for each of the second openings including a conductive island, a constant ratio of conductive surface area to dielectric opening surface area is maintained;
    a handpiece configured to removably receive the treatment tip; and
    a generator configured to generate electromagnetic energy, wherein the conductive layer of the treatment electrode is electrically connected with the generator.

2. The apparatus of claim 1 wherein each conductive island is separated by a gap in the conductive layer from an adjacent portion of the conductive layer surrounding a corresponding one of the second openings and is electrically isolated from the adjacent portion of the conductive layer.

3. The apparatus of claim 1 wherein the first openings are free of conductive islands.

4. The apparatus of claim 1 wherein the treatment electrode includes a plurality of third openings each laterally positioned between the first openings and the second openings, the third openings are larger in size than the first openings, and the third openings are smaller in size than the second openings.

5. The apparatus of claim 1 wherein the treatment electrode includes a solid central region, and the first openings and the second openings are laterally positioned between the solid central region and the outer perimeter.

6. The treatment apparatus of claim 1 wherein when the treatment tip is placed on tissue to be delivered heat treatment via the electromagnetic energy, the generator and treatment electrode produce a uniform temperature increase in the tissue.

7. A treatment apparatus comprising:
    a treatment tip including a treatment electrode and a dielectric layer, the treatment electrode comprising a planar conductive layer with an outer perimeter defining a solid frame, a plurality of first openings extending through the conductive layer, and a plurality of second openings extending through the conductive layer, and the first openings being smaller in size than the second openings, wherein the second openings are located between the outer perimeter and the first openings such that the second openings are not coincident with the first openings, wherein the conductive layer is in contact with the dielectric layer, and the conductive layer includes a conductive island inside one or more of the second openings
    a handpiece configured to removably receive the treatment tip; and
    a generator configured to generate electromagnetic energy, wherein the conductive layer of the treatment electrode is electrically connected with the generator.

8. The apparatus of claim 7 wherein each conductive island is separated by a gap in the conductive layer from an adjacent portion of the conductive layer surrounding a corresponding one of the second openings and is electrically isolated from the adjacent portion of the conductive layer.

9. The apparatus of claim 7 wherein the treatment electrode includes a solid central region, and the first openings and the second openings are positioned between the solid central region and the outer perimeter.

10. The treatment apparatus of claim 7 wherein when the treatment tip is placed on tissue to be delivered heat treatment via the electromagnetic energy, the generator and treatment electrode produce a uniform temperature increase in the tissue.

11. The treatment apparatus of claim 7 wherein the second openings increase in size closer to the outer perimeter.

12. The apparatus of claim 7 wherein the first openings are free of conductive islands.

13. The apparatus of claim 7 wherein the treatment electrode includes a plurality of third openings each laterally positioned between the first openings and the second openings, the third openings are larger in size than the first openings, and the third openings are smaller in size than the second openings.

14. The apparatus of claim 7 wherein a size of the conductive islands relative to the associated second openings is correlated such that the area of exposed dielectric layer is constant for each of the second openings.

15. A method of operating a tissue treatment apparatus, the method comprising:
    moving a handpiece that removably receives a treatment tip of the tissue treatment apparatus proximate to a tissue surface, the treatment tip including a treatment electrode with a dielectric layer;
    contacting a surface of the treatment electrode on the treatment tip with the tissue surface, the treatment electrode including a conductive layer with an outer perimeter, a plurality of first openings extending through the conductive layer, and a plurality of second openings extending through the conductive layer, and the first openings being smaller in size than the second openings, wherein the second openings are located between the outer perimeter and the first openings, and wherein the second openings increase in size closer to the outer perimeter, wherein the conductive layer is in contact with the dielectric layer, and the conductive layer includes a conductive island inside at least some of the second openings, with the conductive islands increasing in size closer to the outer perimeter such that for each of the second openings including a conductive island, a constant ratio of conductive surface area to dielectric opening surface area is maintained;
    generating electromagnetic energy with a generator that is electrically connected to the conductive layer; and
    capacitively transferring the electromagnetic energy from the conductive layer of the treatment electrode to tissue beneath the tissue surface with a local capacitance that depends upon a position of the conductive layer of the treatment electrode relative to the tissue surface, thereby providing heat treatment to the tissue beneath the tissue surface.

16. The method of claim 15 wherein the local capacitance across a surface of the conductive layer decreases closer to the outer perimeter.

17. The method of claim 15 wherein the treatment electrode has a geometrical center, and capacitively transferring the electromagnetic energy from the conductive layer of the treatment electrode to the tissue comprises:
   capacitively transferring electromagnetic energy to the tissue proximate to the outer perimeter from a first portion of the conductive layer, which is perforated by the plurality of second openings to have a first amount of conductor per unit area; and
   capacitively transferring electromagnetic energy to the tissue proximate to the geometrical center from a second portion of the conductive layer, which is perforated by the plurality of first openings to have a second amount of conductor per unit area smaller than the first amount of conductor per unit area.

18. The method of claim 15 wherein the treatment electrode has a geometrical center, and capacitively transferring the electromagnetic energy from the conductive layer of the treatment electrode through the dielectric layer to the tissue comprises:
   capacitively transferring electromagnetic energy to the tissue proximate to the outer perimeter from a portion of the conductive layer perforated with the plurality of second openings; and
   capacitively transferring electromagnetic energy to the tissue proximate to the geometrical center from a solid central region of the conductive layer.

19. The method of claim 15 wherein the electromagnetic energy is capacitively transferred from the conductive layer of the treatment electrode through the dielectric layer to the tissue.

* * * * *